United States Patent [19]
Szilágyi et al.

[11] Patent Number: 4,873,348
[45] Date of Patent: Oct. 10, 1989

[54] OXYPRICIN, A NEW ANTIBIOTIC
[75] Inventors: Imre Szilágyi; Gyula Dékány; Judit Frank; Gábor Horváth; Gábor Kulcsár, all of Budapest, Hungary
[73] Assignee: Chinoin Gyogyszer es Vegyeszeti Termekek Gyara R.T., Budapest, Hungary
[21] Appl. No.: 834,333
[22] PCT Filed: May 31, 1985
[86] PCT No.: PCT/HU85/00034
§ 371 Date: Mar. 10, 1986
§ 102(e) Date: Mar. 10, 1986
[87] PCT Pub. No.: WO85/05621
PCT Pub. Date: Dec. 19, 1985

[30] Foreign Application Priority Data
May 31, 1984 [HU] Hungary ................. 2125/84
Jul. 26, 1984 [HU] Hungary ................. 2869/84
[51] Int. Cl.$^4$ ........................... C07D 313/04
[52] U.S. Cl. ........................... 549/271
[58] Field of Search ........................... 549/271

[56] References Cited
U.S. PATENT DOCUMENTS
4,070,376  1/1978  LeMahieu et al. ................. 549/271

OTHER PUBLICATIONS
Aberhart, J., et al., *J. Am. Chem. Soc.* (1970) 92, pp. 5816–5817.
Aberhart, J., et al., *J.C.S. Perkin* I (1974), pp. 816–826.

*Primary Examiner*—Richard L. Raymond
*Assistant Examiner*—Mark W. Russell
*Attorney, Agent, or Firm*—Herbert Dubno; Jonathan Myers

[57] ABSTRACT
Oxypricin, an antibiotic of the Formula (II)

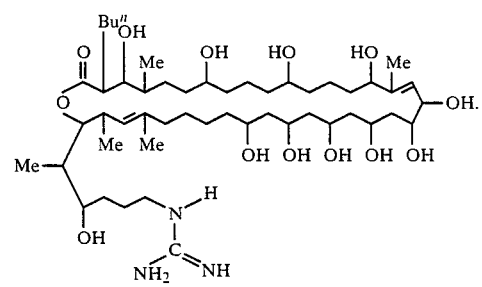

having antibiotic activity is disclosed.

5 Claims, No Drawings

4,873,348

OXYPRICIN, A NEW ANTIBIOTIC

CROSS REFERENCE TO RELATED APPLICATIONS

This application is a national phase application corresponding to PCT/HU85/00034 filed 31 May 1985 based upon Hungarian national applications 2125/84 of 31 May 1984 and 2869/84 filed 26 July 1984 under the International Convention.

FIELD OF THE INVENTION

The present invention relates to different components of primycin obtained by the separation of primycin-mixture and to a process for the separation of these components from the antibiotic complex. The invention also relates to a synergistic pharmaceutical composition comprising the said components and to a process for the preparation thereof.

BACKGROUND OF THE INVENTION

The primycin antibiotic complex can be obtained from the culture of strain *Thermopolyspora galeriensis* belonging to the species of Streptomycetae, its preparation by fermentation is described by Hungarian patent specification No. 153,593.

Primycin is an antibiotic of macrolide type which is characterized in the prior art (J. Chem. Soc., Perkin I. page 816, 1974) by one single formula: [5-{18-($\alpha$-D-arabinofuranosyloxy)-2-butyl-3,7,11,15,19,21,23,25,27-nonahydroxy-4,16,32,34-tetramethyl-1-oxo-oxacyclohexatriaconta-16,32-diene-35-yl}-4-hydroxyhexyl]-quanidinum sulphate.

Primycin is a very effective antibiotic which can be widely used; it is effective primarily against gram-positive bacterias but also against the polyresistant human pathogenic strains. Resistance has not developed against it as yet.

Our former experiments have already referred to the fact that the primycin composition obtained by fermentation is not a homogeneous substance. Recent developments of chromatography have enabled us to subject the primycin substance mixture to a more detailed searching examination.

DETAILED DESCRIPTION OF THE INVENTION

We have now discovered that the primycin composition obtained by fermentation comprises three major and six minor components and the process of our invention is suitable for the qualitative and micropreparative separation of these components. Surprisingly we have also found that components enhance each other in effect, i.e. they show synergistic activity in various combinations.

We targeted our efforts at separating and isolating the different components of the antibiotic complex produced by strain *Thermopolyspora galeriensis*. Several chromatographic methods were tested and it was found that thin-layer and coloumn chromatography are the most effective for this purpose.

In the field of thin-layer chromatography (TLC) the use of commercial chromatographic plates, with silica gel adsorbent layer thereafter the high performance thin-layer chromatographic plates with suitable solvent system resulted in the separation of the components with surprisingly high resolution.

According to a preferred embodiment of the separation process of our invention the stock solution of the fat-free, crude, semi-half or pure product derived from the mycelium of strain *Thermopolyspora galeriensis* is applied onto a TLC chromatoplate, developed, the spots thus obtained are detected and the major and/or minor components of the antibiotic complex are separated.

For the preparation of the stock solution of the crude, semi-half or pure product recovered from the culture medium aqueous solutions of alcohols of 1 to 4 carbon atoms or a mixture thereof, preferably a 25:25:50 by volume mixture of ethanol:n-butanol:water is used. 0.5 to 1 w/v % solution is prepared by the aid of the above mixture and 50 to 200 $\mu$g of the substance to be examined is applied to the plate.

In our experiments we used a commercial silica gel chromatographic plate typ Kieselgel 60 $F_{254}$ (size: 20×20 cm, thickness of the silica gel layer: 0.2 mm). Several solvent mixtures were tested on this plate in order to achieve the best separation of the primycin mixture.

The best separation can be attained when the eluent used comprises halogenated hydrocarbons, organic acids, alcohols, water, and preferably aldehydes.

The following solvents can be used as eluent: halogenated aliphatic hydrocarbons (e.g. chloroform, dichloromethane), organic acids, preferably aliphatic carboxylic acids of 1 to 4 carbon atoms (e.g. formic acid, acetic acid), halogenated aliphatic carboxylic acids (e.g. monochloro-, dichloro- and trichloroacetic acid, trifluoroacetic acid), aromatic carboxylic acids (e.g. benzoic acid), organic sulphonic acids (e.g. methanesulphonic acid, toluenesulphonic acid), alcohols, preferably aliphatic straight or branched alcohols of 1 to 10 carbon atoms (e.g. methanol, ethanol, n-butanol, isopropanol), aldehydes, preferably aliphatic aldehydes of 1 to 4 carbon atoms (e.g. 36% formaldehyde) or aqueous mixtures thereof.

For the separation of the components of the primycin antibiotic complex the following solvent systems proved to be the most effective:

I. the upper layer of a 60:10:30 mixture of n-butanol, glacial acetic acid and water,
II. a 75:2:8:15 mixture of n-butanol, methanol, glacial acetic acid and water,
III. the lower layer of a 45:30:15:20 mixture of chloroform, methanol, glacial acetic acid and water,
IV. a 50:35:14:1 mixture of chloroform, methanol, formic acid and water.
V. a 130:53:6:9:3:3 mixture of chloroform, methanol, formic acid, water, formaldehyde and n-butanol,
VI. a 160:53:6:9:3:3 mixture of chloroform, methanol, formic acid, water, formaldehyde and n-butanol,
VII. 15 parts by weight of monochloroacetic acid dissolved in a 125:53:9:3:3 mixture of chloroform, methanol, water, formaldehyde and n-butanol,
VII. 15:2:1 mixture of the solvent system III, chloroform and methanol.

The solvent mixtures I and II are of higher capacity, while solvent mixtures III, IV, V, VI, VII and VIII are more selective and preferably the developing time is shorter which is preferable from the point of view of industrial serial tests. Solvent systems IV, V and VI are chemically metastabile due to the formation of methylformate, while solvent III is physically metastabile. According to its isothermic curves system IV can be used up within 16 to 24 hours calculated from its preparation, systems V, VI, VII and VIII can be used at once after adding the components to each other, while system III can be preserved for 1 week if 1 to 2% methanol is added. Solvent systems IV, V, VI, VII and VIII are preferred. In eluent IV the suitable separation can be achieved if the development is carried out twice as the $R_f$ values of the different components of the antibiotic complex are very similar, while even one development can lead to appropriate separation if solvent systems V, VI or VII are used. The most preferred solvent systems are systems V, VI, VII and VIII. Solvent V can be used for normal chromatographic plates for thin layer chromatography, while eluent VI can be applied for HPTLC plates. Solvent system VII is suitable for the impregnated plates, and solvent mixture VIII is preferably used for the Lobar-column.

The components of the primycin substance mixture separated by thin layer chromatography can be detected by chemical methods and/or bioautography.

For chemical detection sulfuric acidic vanillin, chlorotoluidine, phosphomolybdic acid, benzidine, modified Sakaguchi reagent and/or ethanolic sulfuric acid known from the prior art and/or heat treatment are the most effective, giving a specific characteristic and sensitive color reaction. The spots can be located preferably by immersing the development chromatoplates into suitable reagents and after drying the chromatograms can be evaluated by Shimadzu densitometer in some cases.

The bioautographic development is carried out as follows:

The plate is cut into strips perpendicularly by the side of the spots after the thin-layer chromatographic development and chemical detection. In the meantime an agar plate is made and inoculated by *Bacillus subtilis* ATCC 6633. The cut band is pressed onto the agar plate after the spots are marked on the opposite side or the strip is perpendicularly cut into two pieces and only one of the pieces is pressed onto the agar sheet. Thereafter the agar plates are incubated at 37° C. for 20 to 24 hours. Upon rising out from the thermostat the spots where the bacteria could not grow can be well observed. The spots responsible for the inhibition of the growth of the bacteria can be identified on the basis of the marked opposite side of the strip if the whole strip was used, or on the basis of the other half-band placed by the side of the original strip.

The efficiency of the separation can be enhanced by using an HPTLC plate. Then solvent system VI is used as eluent in order to provide appropriate separation.

Similarly excellent separation can be obtained when Kieselgel 60 $F_{254}$ chromatographic plate impregnated with a suitable metal salt, preferably silver salt is used insted of the hardly available and expensive HPTLC plate. In the course of the impregnation the chromatographic plate is plunged into the aqueous and/or organic solvent e.g. acetonitrilic solution of the metal salt, preferably 20% aqueous solution is used. Preferably silver salts, e.g. silver nitrate, iron salts, e.g. iron(II)-phosphate can be used as metal salts. The surface humidity of the impregnated layer is dried off thereafter the plate is activated at 120° C. for a hour with the exclusion of light. For developing the chromatogram solvent systems V and VI are very useful in this case as well, but the best separation can be achieved when solvent system VII is used. The efficiency of the separation is highly enhanced in this system by the fact that the difference of the $R_f$ values of the individual components increases.

It was found that primycin is a mixture of three major components ($A_1$, $B_1$, $C_1$) and more minor components.

The individual components crystallize together depending on the solubility conditions. The percentile composition of the antibiotic complex can be influenced by changing the conditions of the fermentation (nutrient medium, cultivating time and temperature, degree of aerating etc.).

The advantages of the thin-layer chromatography elution was improved by working out the preparative separation of the primycin mixture by column chromatography. The partition and adsorption coloumn chromatography was tested.

According to our invention the partition column chromatographic separation is carried out by using a solid carrier (Sephadex LH-20) and a counter current (Droplet Counter Current Chromatography, further referred to as DCCC).

The same solvent systems can be used for this method as for the thin-layer chromatography, i.e. two layer solvent systems containing organic acids, and/or chlorinated hydrocarbons and/or alkanols of 1 to 4 carbon atoms and/or water. Solvent system I is preferred (stationary phase) wherein the solid carrier (Sephadex LH-20) is swelled for two days, thereafter it is filled into the chromatographic column and washed with the lower phase of a 30:10:60 mixture of n-butanol, glacial acetic acid and water (mobile phase). Primycin is dissolved in a 20:1 mixture of the mobile and stationary phase, filtered on a glass filter and applied to the column. The lower, mobile phase is used as eluent preferably using a peristaltic pump and a collector. The composition and purity of the fractions are controlled by thin-layer chromatography, the separation is checked by viewing the chromatograms under ultraviolet light at 206 nm.

The fractions of the same composition are combined and exposed to vacuum distillation and the yields are determined. A 90 to 95% of the product applied to the column is recovered.

The eluate containing mainly major components $A_1$, $B_1$ and $C_1$ is further purified by chromatography.

Component $A_1$ was chromatographed with solvent system I, component $B_1$ was obtained with a solvent containing benzene, n-butanol, methanol, glacial acetic acid and water, while component $C_1$ was separated by the DCCC method with a solvent system composed from chloroform, methanol, glacial acetic acid and water.

It was found that the components of the primycin mixture can be most preferably separated by column chromatography optionally under gentle pressure using the suitable silica gel packing. The following columns were tested: silica gel column filled by us; the ready-to-use Lobar column (Merck), a column filled with silica gel impregnated with a soluble metal salt (similarly to the thin-layer chromatographic plate).

The efficiency of the separation is highly enhanced if the Lobar column is used or in lack of this column, the column is filled with impregnated silica gel instead of a coloumn filled with simple silica gel. A slight overpressure (1.1 to 5.0 atm) can be useful in the case of the Lobar column as well as the column filled with impregnated gel.

In the course of impregnation the silica gel is mixed with a suitable metal salt; preferably it is suspended in the solution of the metal salt prepared with an organic solvent, thereafter the solvent is optionally removed and the impregnated silica gel can be used as the packing of the column. The column is filled with impregnated silica gel suspended in an organic solvent, preferably halogenated aliphatic hydrocarbon (e.g. chloroform) and compacted by slight overpressure (1.1 to 2.5 atm). If a silver salt is used as metal salt, it is desirable to protect the column from light in order to prevent the reduction of the silver salt.

The primycin mixture to be separated or the separated components thereof is applied onto the top of the column, dissolved in the solvent mixture used as eluent and adsorbed by slight overpressure.

The substance mixture to be separated can be industrial primycin sulphate or another primycin salt preferably primycin acetate or primycin monochloroacetate prepared from primycin sulphate according to the Hungarian patent specification No. 257/84.

Solvent systems V, VI, VII and VIII can be used as solvents. The best separation then can be achieved if solvent mixture V, VI or VIII is used for eluting the Lobar column, while solvent mixture VII is the most preferable for eluting the column filled with silica gel impregnated with metal salt.

Fractions of the same volume are collected by a constant flow rate and the composition thereof is controlled by thin layer chromatography. The fractions containing the substance of the same $R_f$ value are combined and the individual components are recovered by solvent precipitation.

As a result of the separation by column chromatography the following components were isolated:

$A_1$ = chinopricin ($R_f$ = 0.29)
$A_2$ = midopricin ($R_f$ = 0.31)
$A_3$ = metipricin ($R_f$ = 0.33)
$C_1$ = oxipricin ($R_f$ = 0.35)
$C_2$ = oximipricin ($R_f$ = 0.37)
$C_3$ = oximetipricin ($R_f$ = 0.39)
$B_1$ = hydropricin ($R_f$ = 0.54)
$B_2$ = hymipricin ($R_f$ = 0.56)
$B_3$ = hymetipricin ($R_f$ = 0.58)

The separated components were tested and the following results were obtained:

1. $A_1$ = chinopricin ($R_f$ = 0.29)

Molar weight measured by fast atom bombardment mass spectrometry method (FAB-MS) is 1078. The isolated component $A_1$ was found to be chemically uniform by analysing with thin-layer chromatography and FAB-MS. Its structure determined on the basis of the molecular weight, of the IR and of the $^1H$ and $^{13}C$ NMR one- and two dimensional spectras is represented by formula I.

Molar weight (FAB-MS): 1092 and 1106.

On the basis of the molar weight, of chemical method and of $^1H$ and $^{13}C$ NMR one and two dimensional spectroscopic examinations. If was found that components $A_2$ and $A_3$ are the homologues of component $A_1$, the side chain of $A_2$ is longer by a methylene group, while the side chain of $A_3$ is longer by an ethylene group than that of $A_1$.

3. $C_1$ = oxypricin ($R_f$ = 0.35)

Molar weight: 946 (FAB-MS)

On the basis of the above analytical methods compound $C_1$ can be represented by the following formula II.

(II)

The difference between component $C_1$ and $A_1$ is that instead of the sugar moiety a hydroxyl group is bound to the carbon atom in position 18.

4. $C_2$ = oxymipricin ($R_f$ = 0.37) and $C_3$ = oxymetipricin ($R_f$ = 0.39).

Molar weight (FAB-MS): 960 and 974.

On the basis of the above analytical methods it was found that the side chain of component $C_2$ is longer by a methylene group, while the side chain of $C_3$ is longer by an ethylene group than that of $C_1$.

5. $B_1$ = hydropricin ($R_f$ = 0.54)

Molar weight (FAB-MS): 930.

On the basis of the above analytical methods the compound can be represented by the formula III (III)

(I)

2. $A_2$ = midopricin ($R_f$ = 0.31) and $A_3$ = methipricin ($R_f$ = 0.33)

wherein instead of the sugar moiety a hydrogen is bound to the carbon atom being in position 18.

6. $B_2$=hymipricin ($R_f$=0.56) and $B_3$=hymetipricin ($R_f$=0.58)

Molar weight (FAB-MS): 944 and 960.

On the basis of the above analytical methods it was found that the side chain of component $B_2$ is longer by a methylene group and the side chain of component $B_3$ is longer by an ethylene group than that of $B_1$.

The usual physical constants (melting point, elemental analysis data, optical activity, UV and IR specra, etc.) are not characteristic for the individual compounds. E.g. the melting point of the single components is 160° to 170° C., the melting point of their mixture is 167°–168° C. The elemental analysis data are also not characteristic for the individual components as they are of similar structure, high molar weight, therefore the differences in the elemental analysis data are in the range of measuring error. The main part of the primycin mixture comprises components $A_1$, $B_2$ and $C_3$ therefore they are called major components. The other components being present in smaller amount are called minor components.

The primycin components were isolated in the form of sulfate of other salts different from sulfate, preferably acetate or monochloroacetate depending on the starting primycin mixture.

The sulfate salts of the isolated primycin components can be transferred into other salts by the aid of different organic or inorganic acids as is described in the Hungarian patent application No. 2571/84.

The spectra of the antimicrobial activity of the primycin mixture and the three minor components ($A_1$, $B_1$ and $C_1$) is shown by Table 0 (see later page 24). The table contains the MIC values (μg/ml) measured on human pathogenic polyresistant strains. The different values refer to the fact that the three major components probably exert their antimicrobial activity in a different manner, they attack different points of the microorganism.

Surprisingly we found that the components strengthen each other's effect, i.e. they show potentiather synergism. On the basis of the synergistic effect and the supposed different attacking point of the major components the following advantageous effects can be achieved by using the composition of the components:

1. By simultaneously attacking the metabolism of the pathogens at different points the "cidal-effect" i.e. the killing of the microorganism can be attained more safely which is much more preferable than the static effect, i.e. the simple inhibition of the growth of the microorganisms.

2. If different routes of metabolism are simultaneously attacked, the resistance against the active ingredient combination can not develop or must develop more slowly.

3. The amount of the individual components used can be highly decreased. It results in the advantage that the harmful side-effects diminish or completely disappear due to the administration of less active ingredient. This effect is very advantageous from thereapeutical points of view. When less active ingredient is used the expenses also decrease, which is favorable from economical points of view.

In the synergistic composition according to our invention the major components ($A_1$, $B_1$, $C_1$) and other, minor components of primycin and derivatives thereof, preferably salts can be used. A composition can comprise two or three or more different components.

If two major components are used in the composition the weight ratio of the components is in the range of 5:95 to 25:75, while if three components are used, then the weight ratio of the components is in the range of 4:3:3 to 7:1:2. The preferred embodiments of the synergistic compositions according to the invention are illustrated by the following examples, wherein the MIC values measured by using different microorganism strains and the degree of the additive and synergistic effect are also indicated. Under the term "additive effect" we mean that the effect of the components is summarized, thus e.g. by adding the half of the MIC value of the one component to the half of the MIC value of the second component, the MIC value of the combination of the two active ingredients is obtained. When the antimicrobial activity exceeds the additive effect due to the favorable interaction of the components, potentiative synergism appears and the effect thus obtained is the synergistic effect..

The MIC values were determined in Difco-Bouillon culture medium. The evaluation was carried out after incubating at a temperature of 37° C. for 24 hours, and $5 \cdot 10^5$/ml spores were inoculated. In Examples 13 to 25 the 197 cases express illustrate that the composition containing more active ingredients is of synergistic activity, thus only a part or a small portion of the original quantity of the active ingredients has to be administered in order to achieve the same effect.

The primycin components according to the invention can be administered alone or mixed with each other, optionally together with other pharmaceutically active ingredients. They can be administered alone, but are generally administered with a pharmaceutical carrier selected on the basis of the route of administration and standard pharmaceutical practice. The active ingredient can be administered in solid dosage forms, such as capsules, tablets, dragees, suppositories, semi-solid forms such as ointments or gels or liquid dosage forms such as injectable solutions, suspensions or syrups. The preferred dosage forms are the gels, ointments, surgical dusting powders, injections, suspensions and combinations of powder ampoules-solvent ampoules.

The compositions according to our invention can be administered orally, parenterally, rectally or topically (e.g. ointments). They contain usual pharmaceutical carriers (e.g. magnesium carbonate, magnesium stearate, starch, talc, water, etc.) or novel carriers, e.g. cyclodextrin and optionally excipients, disintegrating agents, emulsifiers etc.

The dosage forms suitable for oral administration may be e.g. tablets, dragees or capsules. The synergistic compositions containing more active ingredient according to the invention can be also used in veterinary therapeutics e.g. in the form of a liquid mixed to the feedstuff. The dosage forms suitable for parenertal administration can be aqueous emulsions, solutions or suspensions. Dusting powders, ointments, aqueous or oily emulsions or bandages impregnated with these emulsions or suspensions or sprays can be used for topical administration.

The invention is illustrated by the following, non-limiting examples.

EXAMPLE 1

Separation of Primycin on Kieselgel by Thin-Layer Chromatography by Double Development 0.5% solution of primycin-complex is prepared with a 1:1:2 mixture of n-butanol, ethanol and water or methanol. 10 μl (50 μg of active ingredient) of the solution is dropped onto the Kieselgel plates (DC-Plastikfolie, Kieselgel 60 $F_{254}$ or DC-Alufolie Kieselgel 60, produced by Merck, layer thickness: 0.2 mm). Solvent system IV is used as eluent and the chromatogram is developed for a distance of 16 cm. The development is repeated. The spots are visualized by a color reaction and the evaluation is carried out by densitometry at 590 nm. The biological activity is detected by bioautographic assay.

The composition of the culture medium used in the course of the bioautographic assay is as follows:

| | |
|---|---|
| Beef extract (Difco) | 3 g |
| Bacto pepton (Difco) | 5 g |
| Sodium chloride | 5 g |
| Disodium hydrogenphosphate | 10 g |
| Potassium dihydrogenphosphate | 1 g |
| Bacto agar (Difco) | 18 g |
| Distilled water to | 1000 ml |

The culture medium is incubated at 121° C.; thereafter the pH is adjusted to 8.0. 130 ml of culture medium of a temperature of 53° C. are filled into sterile glass dishes (18×25 cm) and Bacillus subtilis ATCC 6633 spore suspension is added in a ratio of 1:2,000. Strips of 5 mm width are cut from the chromatograms, dried solvent-free and superposed to the agar plate and incubated for 18 to 24 hours at a temperatue of 37° C.

EXAMPLE 2

Separation of the Primycin Mixture on Kieselgel by Single Thin-Layer Chromatographic Development The procedure of Example 1 is followed except that solvent mixture V is used as eluent therefore the development is carried out once.

EXAMPLE 3

Separation of the Primycin Mixture on HPTLC Plate with Single Development

4 μl (20 μg active ingredient) of the 0.5% solution prepared according to Example 1 is applied onto a HPTLC (Merck) plate and developed for a distance of 18 cm. The further steps are the same as described in Example 1.

EXAMPLE 4

Separation of Primycin Mixture on Impregnated Kieselgel Plate with Single Development The procedure of Example 1 is followed except that solvent mixture VII is used for the development and the Kieselgel 60 $F_{254}$ plate is impregnated with a metal salt according to the method described hereinabove before use.

The further steps are the same as described in Example 1.

EXAMPLE 5

Separation of the Primycin Mixture on Preparative Thin Layer Chromatographic Plate 2 ml of the 1% solution of the sample to be examined is applied onto a PSC-Fertigplatten, Kieselgel 60 $F_{254}$ (Merck) plate. The plates are developed by solvent system IV more times. If a 3-3 cm wide strip on the left and the right side of the glass plates is plunged into pre-heated Sakaguchi reagent, the spots appeared as vivid red spots at room temperature. The distinct fractions are scraped off and eluted in a micropercolator with 10% acetic acidic methanol until no reaction can be observed upon adding sulphuric acidic vanillin. The eluate is distilled in vacuo, the dry residue is dissolved in solvent system I and extracted with distilled water of fifth part volume four times.

The components of the antibiotic are in the upper layer, while the "layer dead weight" is in the lower phase. The components obtained by evaporating the upper phase are further purified according to a method of Example 1.

EXAMPLE 6

Separation of the Components "A" of Primycin by Partition Column Chromatography Solvent system used:
stationary phase: solvent system I
mobile phase: the lower phase of a 30:10:60 mixture of n-butanol, glacial acetic acid and water Preparation of the column:
720 g of Sephadex LH-20 gel is swollen in 3 l of solvent system I for 1 day. The suspension is filled to a chromatographic column (58×1150 mm), settled, thereafter washed with 1.5 l of mobile phase.

Chromatographic procedure:
2 g of primycin are dissolved in a mixture of 300 ml of mobile phase and 15 ml of stationary phase, the solvent is filtered and applied onto the column. The elution is carried out by the aid of the mobile phase with a flow rate of 50 to 60 drops/minute.

Generally fractions of 17 ml volume (=800 drops) are collected and the elution is continued until 300 to 400 fractions are obtained.

The fixed phased Sephadex LH-20 column can be used up for 3 to 4 times if the phase is changed. The gel can be regenerated as follows: it is suspended in acetone, filtered, refluxed for 2 hours with acetone in the vapor space and thereafter dried. The substances being in the different fractions are identified by thin-layer chromatography and UV spectroscophy.

Isolation of the components:
The fractions which are found to comprise the same substance on the basis of the analysis data (UV and TLC) are combined. The residue obtained after evaporation of the solvent is dissolved in a 2:1 mixture of methanol and benzene and evaporated again.

Thus 743 mg of a mixture of the components A and a mixed fraction of 570 mg comprising components A and C are obtained. Components B remain on the column in this system, they can be dissolved by solvent system I, 480 mg of components B can be obtained. A further chromatography of component mixture A under the above conditions results in major component $A_1$ in a purity higher than 98%.

EXAMPLE 7

Separation of Components B of Primycin by Partition Column Chromatography

The components B obtained as described in Example 6 are further purified with a chromatographic method described hereinabove except that the so-called "B-selective" solvent system is used as eluent. Thus major component $B_1$ can be obtained with a purity higher than 96%.

The composition of the "B-selective" solvent system is as follows:
stationary phase: the upper phase of a 1:41:10:5:43 mixture of benzene, n-butanol, methanol glacial acetic acid, water,
mobile phase: the lower phase of a 1:24:10:5:60 mixture of benzene, n-butanol, methanol, glacial acetic acid and water

EXAMPLE 8

Separation of the Components of Primycin by DCCC (Droplet Counter Current Chromatography)

The mixed fractions obtained in Example 6 are further purified by DCCC.

The solvent system used is as follows:
stationary phase: the lower phase of a 26:39:9:26 mixture of chloroform, methanol, glacial acetic acid and water,
mobile phase: the upper layer of the same mixture
Elution:

The solvent system is stirred for 2 hours, left to stand for 16 hours and the phases are separated. The DCCC instrument (ID=2.0 mm, 300 tubes) is filled with the lower phase (stationary phase). 130 mg of the substance to be examined are dissolved in 12 ml of upper phase (mobile phase), filtered and pumped to the container. The elution is carried out by the aid of the upper phase, under an overpressure of 1.7 to 1.8 atm with a flow rate of 15 ml/hour and fractions of 3.7 ml volume (=220 drops) are collected. Thus major component $C_1$ is obtained in a purity of 90%.

EXAMPLE 9

Separation of the Components of Primycin by Adsorptive Column Chromatography on Silica Gel Impregnated with a Metal Salt Preparation of the column:

In a solution of 40 g of silver nitrate and 500 ml of acetonitrile 200 g of Kieselgel $HF_{254}$ silica gel are suspended thereafter the solvent is evaporated in vacuo. The impregnated silica gel is suspended in 500 ml of chloroform and filled into the chromatographic column. In order to promote the settling and the compaction a slight overpressure (1.1 to 2.5 atm) is used until the height of the packing bed settles. In order to avoid the reduction of silver nitrate due to light the column is covered with aluminum foil.

Chromatographic procedure:

400 mg of primycin are dissolved in 12 ml of solvent system VII freshly prepared. The solution is adsorbed by the aid of slight overpressure (1.1 atm) onto the packing bed. 30 ml of eluent (solvent system VII) are applied onto the top of the packing and the elution is started with a flow rate of 1.1 ml/minute under an overpressure of 1.5 to 2.5 atm.

Working up:

The substances being in the fractions are identified by thin-layer chromatography. 10 $\mu l$ of each fractions are applied to the starting points of Kieselgel 60 $F_{254}$ (Merck) plates and developed for a distance of 16 cm in an unsaturated chamber with solvent system V. The spots are located by development with chlorotolidin reagent and/or sulfuric acid and/or heat treatment after drying with cold air.

The fractions comprising the same substance are combined and the primycin component is precipitated by adding ether. The solid substance precipitated is filtered off and washed with some acetonitrile and ether. The residue is dissolved in the upper layer of a 4:1:5 mixture of n-butanol, acetic acid and water and washed with 5 ml of water three times. The solvent is evaporated from the substance being in the separated upper layer under vacuo, the residue is triturated with ether, filtered and dried under vacuo.

Thus
135 mg of component $A_1$=chinopricin,
30 mg of component $A_2$=midopricin,
40 mg of component $A_3$=metipricin,
20 mg of component $C_1$=oxypricin,
20 mg of component $B_1$=hydropricin
are obtained.

Remark: the major part of the silver nitrate being on the column protected from light can be recovered by washing with acetonitrile and used again.

EXAMPLE 10

Separation of the Components of Primycin by Absorption Coloumn Chromatography on Ready-Made Lobar Column The coloumn used:

Lobar C (Merck) column filled with LiChroprep, preferably two or more columns are joined.

Chromatographic method:

The procedure of Example 9 is followed except that solvent system VIII is used as eluent. 3400 mg of primycin are dissolved in 40 ml of solvent system VIII, thereafter this solution is applied onto the top of a column system containing four columns connected in series.

Working up:

The fractions comprising the same substances are combined, n-butanol in a quantity corresponding to 10% of total volume of the fractions is added and the solutions are evaporated in vacuo at a maximal temperature of 45° C. The solid residue is triturated with ether and filtered.

Thus
1100 mg of component $A_1$=chinopricin,
110 mg of component $A_2$=midopricin,
80 mg of component $A_3$=metipricin,
110 mg of component $C_1$=oxypricin,
20 mg of component $C_2$=oxymipricin,
15 mg of component $C_3$=oxymetipricin,
150 mg of component $B_1$=hydropridin,
50 mg of component $B_2$=hymipricin,
40 mg of component $B_3$=hymetipricin
are obtained.

EXAMPLE 11

Preparation of the Sulfate Salts of the Components of Primycin

The procedure of Example 10 is followed except that 5 ml of methanol and 0.3 ml of 1N sulfuric acid are added to the combined fractions. The precipitation is completed by adding 300 ml of ether.

Thus the primycin components of Example 10 are obtained in the form of sulfate salt.

EXAMPLE 12

Preparation of the Salts of the Components of Primycin Different from Sulfate

From the sulfate salts of the components of primycin other salts different from the sulfate salt are prepared by adding barium salts according to the process of Hungarian patent application No. 2571/84.

Thus the salts of the primycin components different from sulfate are obtained in the form of e.g. formate, acetate, monochloroacetate, oxalate, benzoate, tosylate, perchlorate, chloride etc.

The antimicrobial activity of the primycin complex and the components thereof is tested on different microorganism strains. The results are listed in Table O.

TABLE O

The antimicrobial spectra of the major components of primycin
(Inoculation: $5 \times 10^5$/ml, incubation at 37° C. for 24 hours)

| Human pathogenic polyresistant strains | MIC. (µg/ml) Major Components | | |
|---|---|---|---|
| | $A_1$ | $C_1$ | $B_1$ |
| 1. Staphylococcus aureus CCM.885. | 0.25 | 0.075 | 0.5 |
| 2. Staphylococcus aureus DSM.20231 | 0.05 | 0.05 | 0.1 |
| 3. Staphylococcus aureus CCM.2317. | 0.25 | 0.05 | 0.1 |
| 4. Staphylococcus aureus CCM.2326. | 0.25 | 0.05 | 0.25 |
| 5. Staphylococcus aureus CCM.2514 | 0.25 | 0.05 | 0.1 |
| 6. Staphylococcus aureus CCM.2515. | 0.25 | 0.025 | 0.1 |
| 7. Staphylococcus epidermidis CCM.2271 | 0.75 | 0.025 | 0.25 |
| 8. Staphylococcus aureus Smith | 0.25 | 0.05 | 0.5 |
| 9. Streptococcus faecalis CCM.1875. | 2.5 | 0.75 | 2.5 |
| 10. Streptococcus agalactiae CCM.5153. | 0.75 | 0.075 | 0.5 |
| 11. Streptococcus agalactiae CCM.5534. | 1.0 | 0.25 | 1.0 |
| 12. Streptococcus disgalactiae ATTC.9926 | 2.5 | 0.5 | 2.5 |
| 13. Bacillus subtilis ATTC.6633. | 0.25 | 0.025 | 0.1 |
| 14. Bacillus cereus CCM.2010. | 0.25 | 0.025 | 0.25 |
| 15. Bacillus licheniformis CCM.2182. | 0.25 | 0.025 | 0.25 |
| 16. Bacillus licheniformis CCM.2205. | 0.25 | 0.025 | 0.25 |
| 17. Bacillus subtilis CCM.1718. | 0.25 | 0.05 | 0.25 |
| 18. Listeria monocytogenes CCM.5576. | 0.5 | 0.075 | 0.25 |
| 19. Micrococcus flavus ATCC.10240. | 0.075 | 0.01 | 0.05 |
| 20. Micrococcus luteus DSM.20030. | 0.05 | 0.01 | 0.075 |
| 21. Sporosarcina ureae DSM.317 | 0.025 | 0.01 | 0.025 |
| 22. Pseudomonas aeruginosa CCM.1960. | 25 | 25 | 25 |
| 23. Pseudomonas fluorescens CCM.2115. | 25 | 25 | 25 |
| 24. Pseudomonas acidoverans CCM.283 | 25 | 25 | 25 |
| 25. Proteus vulgaris CCM.1799. | 50 | 50 | 50 |
| 26. Shigella sonnei CCM.1373. | 50 | 50 | 50 |
| 27. Salmonella typhimurium CCM.5445. | 50 | 50 | 50 |
| 28. Escherichia coli DSM.30038. | 50 | 50 | 50 |

TABLE O/a

The antimicrobial spectra of the primycin antibiotic complex for human pathogenic microorganism strains

| Strains | MIC/µg/ml |
|---|---|
| 1. Bacillus subtilis ATCC.6633. | 0.02 |
| 2. Bacillus subtilis CCM.1718 | 0.1 |
| 3. Bacillus cereus CCM.2010 | 0.1 |
| 4. Bacillus licheniformis CCM.2182 | 0.075 |
| 5. Bacillus licheniformis CCM.2205 | 0.075 |
| 6. Staphylococcus aureus CCM.885. | 0.25 |
| 7. Staphylococcus aureus CCM.2317 | 0.1 |
| 8. Staphylococcus aureus CCM.2514 | 0.25 |
| 9. Staphylococcus aureus CCM.2515 | 0.25 |
| 10. Streptococcus faecalis CCM.1875 | 0.5 |
| 11. Streptococcus agalactiae CCM.5534. | 0.5 |
| 12. Streptococcus dysgalactiae CCM.5548. | 0.5 |
| 13. Streptococcus agalactiae CCM.5153. | 0.5 |
| 14. Mycobacterium tuberculosis typ. hu $H_{37}Rv$. | 0.05 |

TABLE O/a-continued

The antimicrobial spectra of the primycin antibiotic complex for human pathogenic microorganism strains

| Strains | MIC/µg/ml |
|---|---|
| 15. Mycobacterium tuberculosis typ. bovin $E_5$ | 0.8–1.0 |
| 16. Mycobacterium tuberculosis 607 | 0.5 |
| 17. Micrococcus flavus ATCC.10240 | 0.075 |
| 18. Pseudomonas aeruginosa CCM.1960. | 25 |
| 19. Pseudomonas fluorescens CCM.2115. | 25 |
| 20. Pseudomonas acidoverans CCM.283. | 25 |
| 21. Pseudomonas pictorum CCM.284 | 10 |
| 22. Proteus vulgaris CCM.1799. | 25 |
| 23. Shigella sonnei CCM.1373. | 25 |
| 24. Salmonella typhi-murium CCM.5445. | 50 |
| 25. Salmonella cholerae-sus Inst. CCM.5438 Pasteur strain | 50 |
| 26. Escherichia coli DSM.30038 | 50 |
| 27. Escherichia haemolyticus CCM.5863 | 50 |
| 28. Escherichia coli ATCC11775, CMM.5172 cystitis | 50 |
| 29. Escherichia coli lysegenic, CCM.180 colicinogenic | 50 |
| 30. Escherichia coli OTKI.17963 | 25 |
| 31. Escherichia coli OTKI.23473 | 50 |
| 32. Klebsiella pneumoniae CCM.1848 | 50 |
| 33. Serratia Marcescens CCM.303 | 25 |
| 34. Pasteurella multocida CCM.5419 | 25 |
| 35. Vibrio parahaemolyticus CCM.5938 | 25 |
| 36. Candida albicans CBS.562 | 25 |
| 37. Candida tropicalis CBS.433 | 25 |
| 38. Candida pseudotropicalis 372 | 5 |
| 39. Candida krusei K-47 | 10 |
| 40. Cryptococcus neoformans K-16 | 5 |
| 41. Saccharomyces cerevisiae OKI.1282 | 10 |

EXAMPLE 13

Synergistic Composition No. I n (the number of components)=2
the ratio of the components: $A_1:B_1=75:25$
The results are summarized in Table I.
Explanation of the table:
Coloumn I: the MIC value of component $A_1$ (µg/ml),
Column II: the MIC value of component $B_1$
Column III: the MIC value of the composition comprising components $A_1$ and $B_1$
Column IV: the amount of $A_1$ being in the composition related to the MIC value of $A_1$ (%)
Column V: the amount of $B_1$ being in the composition related to the MIC value of $B_1$ (%)
Column VI: (IV+V)/n
Column VII: the additive portion of the antimicrobial activity (IV+V)
Column VIII: the synergistic portion of the antimicrobial activity (100%−VII)

TABLE I

| The sign of the strains examined | Experimental results | | | | | | | |
|---|---|---|---|---|---|---|---|---|
| | I | II | III | IV | V | VI | VII | VIII |
| 1 | 0.25 | 0.5 | 0.2 | 60 | 10 | 35 | 70 | 30 |
| 6 | 0.25 | 0.1 | 0.06 | 18 | 15 | 16.5 | 33 | 67 |
| 8 | 0.25 | 0.5 | 0.2 | 60 | 10 | 35 | 70 | 30 |
| 10 | 0.75 | 0.5 | 0.4 | 40 | 20 | 30 | 60 | 40 |
| 11 | 1 | 1 | 0.8 | 60 | 20 | 35 | 80 | 20 |
| 12 | 2.5 | 2.5 | 1 | 30 | 10 | 20 | 40 | 60 |
| 13 | 0.25 | 0.1 | 0.08 | 24 | 20 | 22 | 44 | 56 |
| 14 | 0.25 | 0.25 | 0.1 | 30 | 10 | 20 | 40 | 60 |
| 15 | 0.25 | 0.25 | 0.08 | 24 | 8 | 16 | 32 | 68 |
| 16 | 0.25 | 0.25 | 0.08 | 24 | 8 | 16 | 32 | 68 |
| 17 | 0.25 | 0.25 | 0.05 | 12 | 5 | 8.5 | 17 | 83 |
| 18 | 0.5 | 0.25 | 0.2 | 30 | 20 | 25 | 50 | 50 |
| 19 | 0.075 | 0.05 | 0.02 | 20 | 10 | 15 | 30 | 70 |

EXAMPLE 14

Synergistic Composition No. II n=2 the ratio of the components: $A_1:B_1=50:5$

The antimicrobial activity of the composition is summarized in Table II

TABLE II

| The sign of the strains examined | I | II | III | IV | V | VI | VII | VIII |
|---|---|---|---|---|---|---|---|---|
| 1 | 0.25 | 0.5 | 0.2 | 40 | 20 | 30 | 60 | 40 |
| 4 | 0.25 | 0.25 | 0.08 | 16 | 16 | 16 | 32 | 68 |
| 5 | 0.25 | 0.1 | 0.08 | 16 | 40 | 28 | 56 | 44 |
| 6 | 0.25 | 0.1 | 0.04 | 8 | 20 | 14 | 28 | 72 |
| 7 | 0.75 | 0.25 | 0.06 | 4 | 12 | 8 | 16 | 84 |
| 8 | 0.25 | 0.5 | 0.2 | 40 | 20 | 30 | 60 | 40 |
| 9 | 2.5 | 2.5 | 1 | 20 | 20 | 20 | 40 | 60 |
| 10 | 0.75 | 0.5 | 0.08 | 5.3 | 8 | 6.6 | 13.3 | 86.7 |
| 11 | 1 | 1 | 0.6 | 30 | 30 | 30 | 60 | 40 |
| 12 | 2.5 | 2.5 | 0.8 | 16 | 16 | 16 | 32 | 68 |
| 13 | 0.25 | 0.1 | 0.08 | 16 | 40 | 28 | 56 | 44 |
| 14 | 0.25 | 0.25 | 0.1 | 20 | 20 | 20 | 40 | 60 |
| 15 | 0.25 | 0.25 | 0.06 | 12 | 12 | 12 | 24 | 76 |
| 16 | 0.25 | 0.25 | 0.06 | 12 | 12 | 12 | 24 | 76 |
| 17 | 0.25 | 0.25 | 0.05 | 10 | 10 | 10 | 20 | 80 |
| 19 | 0.075 | 0.05 | 0.03 | 20 | 30 | 25 | 50 | 50 |
| 20 | 0.05 | 0.075 | 0.03 | 30 | 20 | 25 | 50 | 50 |

EXAMPLE 15

Synergistic Composition No. III n=2 the ratio of the components: $A_1:B_1=25:75$

The experimental results of the antimicrobial activity are summarized in Table III. (The abbreviations are the same as in Table I).

TABLE III

| The strains examined | I | II | III | IV | V | VI | VII | VIII |
|---|---|---|---|---|---|---|---|---|
| 1 | 0.25 | 0.5 | 0.2 | 20 | 30 | 25 | 50 | 50 |
| 4 | 0.25 | 0.25 | 0.1 | 25 | 30 | 27.5 | 55 | 45 |
| 6 | 0.25 | 0.1 | 0.03 | 3 | 22.5 | 11.7 | 25.5 | 74.5 |
| 7 | 0.75 | 0.25 | 0.1 | 3.3 | 30 | 16.7 | 33.3 | 66.7 |
| 8 | 0.25 | 0.5 | 0.2 | 20 | 30 | 25 | 50 | 50 |
| 9 | 2.5 | 2.5 | 1 | 10 | 30 | 20 | 40 | 60 |
| 10 | 0.75 | 0.5 | 0.2 | 6.7 | 30 | 18.4 | 36.7 | 63.3 |
| 11 | 1 | 1 | 0.6 | 15 | 45 | 30 | 60 | 40 |
| 13 | 0.25 | 0.1 | 0.05 | 5 | 37.5 | 21.2 | 42.5 | 57.5 |
| 14 | 0.25 | 0.25 | 0.1 | 10 | 30 | 20 | 40 | 60 |
| 15 | 0.25 | 0.25 | 0.08 | 8 | 24 | 16 | 32 | 68 |
| 16 | 0.25 | 0.25 | 0.08 | 8 | 24 | 16 | 32 | 68 |
| 17 | 0.25 | 0.25 | 0.06 | 10 | 18 | 12 | 24 | 76 |
| 19 | 0.075 | 0.05 | 0.03 | 10 | 45 | 27.5 | 55 | 45 |
| 20 | 0.05 | 0.075 | 0.03 | 15 | 30 | 22.5 | 45 | 55 |

EXAMPLE 16

Synergistic Composition No. IV n=2 the ratio of the components: $A_1:C_1=75:25$

The results relating to the antimicrobial activity of the composition are summarized in Table IV. (The abbreviations are the same as in Example 13 except that component $C_1$ is used instead of $B_1$)

TABLE IV

| The strains examined | I | II | III | IV | V | VI | VII | VII |
|---|---|---|---|---|---|---|---|---|
| 1 | 0.25 | 0.075 | 0.03 | 9 | 10 | 9.5 | 19 | 81 |
| 2 | 0.05 | 0.05 | 0.03 | 45 | 15 | 30 | 60 | 40 |
| 3 | 0.25 | 0.05 | 0.02 | 6 | 10 | 8 | 16 | 84 |
| 4 | 0.25 | 0.05 | 0.03 | 9 | 15 | 12 | 24 | 76 |
| 5 | 0.25 | 0.05 | 0.04 | 12 | 20 | 16 | 32 | 68 |
| 6 | 0.25 | 0.025 | 0.02 | 6 | 20 | 13 | 26 | 74 |
| 7 | 0.75 | 0.025 | 0.01 | 1 | 10 | 5.5 | 11 | 89 |
| 8 | 0.25 | 0.05 | 0.01 | 3 | 5 | 4 | 8 | 92 |
| 9 | 2.5 | 0.75 | 0.8 | 24 | 26.6 | 25.3 | 50.6 | 49.4 |
| 10 | 0.75 | 0.075 | 0.03 | 3 | 10 | 6.5 | 13 | 87 |
| 11 | 1 | 0.25 | 0.2 | 15 | 20 | 17.5 | 35 | 65 |
| 12 | 2.5 | 0.5 | 0.4 | 12 | 20 | 16 | 32 | 68 |
| 13 | 0.25 | 0.025 | 0.02 | 6 | 20 | 13 | 26 | 74 |
| 14 | 0.25 | 0.025 | 0.03 | 9 | 20 | 13 | 26 | 74 |
| 15 | 0.25 | 0.025 | 0.03 | 9 | 30 | 19.5 | 39 | 61 |
| 16 | 0.25 | 0.025 | 0.03 | 9 | 30 | 19.5 | 39 | 61 |
| 17 | 0.25 | 0.05 | 0.03 | 9 | 15 | 12 | 24 | 76 |
| 18 | 0.5 | 0.075 | 0.06 | 9 | 20 | 14.5 | 29 | 71 |
| 19 | 0.0750 | .01 | 0.02 | 20 | 50 | 35 | 70 | 30 |
| 20 | 0.05 | 0.01 | 0.02 | 30 | 50 | 40 | 80 | 20 |

EXAMPLE 17

Synergistic composition No. V n=2 the ratio of the components: $A_1:C_1=50:50$

The results relating to the antimicrobial acitivity of the composition are summarized in Table V. (The abbreviations are the same as in Example 13 except that component $C_1$ is used instead of $B_1$)

TABLE V

| The strains examined | I | II | III | IV | V | VI | VII | VIII |
|---|---|---|---|---|---|---|---|---|
| 1 | 0.25 | 0.075 | 0.04 | 8 | 26.6 | 17.3 | 34.6 | 63.4 |
| 2 | 0.05 | 0.05 | 0.02 | 20 | 20 | 20 | 40 | 60 |
| 3 | 0.25 | 0.05 | 0.02 | 4 | 20 | 12 | 24 | 76 |
| 4 | 0.25 | 0.05 | 0.02 | 4 | 20 | 12 | 24 | 76 |
| 5 | 0.25 | 0.05 | 0.02 | 4 | 20 | 12 | 24 | 76 |
| 6 | 0.25 | 0.025 | 0.01 | 2 | 20 | 11 | 22 | 78 |
| 7 | 0.75 | 0.025 | 0.02 | 1.3 | 40 | 20.6 | 41.3 | 58.7 |
| 8 | 0.25 | 0.05 | 0.01 | 2 | 10 | 6 | 12 | 88 |
| 10 | 0.75 | 0.075 | 0.02 | 1.3 | 13.3 | 7.3 | 14.6 | 83.4 |
| 12 | 2.5 | 0.5 | 0.6 | 12 | 60 | 36 | 72 | 28 |
| 13 | 0.25 | 0.025 | 0.02 | 4 | 40 | 22 | 44 | 56 |
| 14 | 0.25 | 0.025 | 0.02 | 4 | 40 | 22 | 44 | 56 |
| 15 | 0.25 | 0.025 | 0.02 | 4 | 40 | 22 | 44 | 56 |
| 16 | 0.25 | 0.025 | 0.02 | 4 | 40 | 22 | 44 | 56 |
| 17 | 0.25 | 0.05 | 0.04 | 8 | 40 | 24 | 48 | 52 |
| 18 | 0.5 | 0.075 | 0.1 | 10 | 66.6 | 38.3 | 76.6 | 23.4 |

EXAMPLE 18

Synergistic Composition No. VI n=2 the ratio of the components = $A_1:C_1=25:75$

The results relating to the antimicrobial activity of the composition are summarized in Table VI. (The abbreviations are the same as in Example 13 except that component $C_1$ is used instead of $B_1$)

TABLE VI

| The strains examined | I | II | III | IV | V | VI | VII | VIII |
|---|---|---|---|---|---|---|---|---|
| 3 | 0.25 | 0.05 | 0.05 | 5 | 75 | 40 | 80 | 20 |
| 12 | 2.5 | 0.5 | 0.6 | 6 | 90 | 48 | 96 | 4 |

EXAMPLE 19

Synergistic Composition No. VII $n=2$ the ratio of the components: $C_1:B_1=75:25$ The results relating to the antimicrobial acitivity of the composition are summarized in Table VII. (The abbreviations are the same as in Example 13 except that component $C_1$ is used of component $A_1$.)

TABLE VII

| The strains examined | I | II | III | IV | V | VI | VII | VIII |
|---|---|---|---|---|---|---|---|---|
| 1 | 0.075 | 0.5 | 0.04 | 40 | 2 | 21 | 42 | 58 |
| 2 | 0.1 | 0.5 | 0.02 | 15 | 1 | 8 | 16 | 84 |
| 3 | 0.05 | 0.1 | 0.02 | 30 | 5 | 17.5 | 35 | 65 |
| 4 | 0.05 | 0.25 | 0.03 | 45 | 3 | 24 | 48 | 52 |
| 5 | 0.05 | 0.1 | 0.03 | 45 | 7.5 | 26.3 | 52.5 | 47.5 |
| 6 | 0.025 | 0.1 | 0.02 | 60 | 5 | 32.5 | 65 | 35 |
| 8 | 0.05 | 0.5 | 0.02 | 30 | 1 | 15.5 | 31 | 69 |
| 10 | 0.075 | 0.5 | 0.06 | 60 | 3 | 31.5 | 63 | 37 |
| 11 | 0.25 | 1 | 0.2 | 60 | 5 | 32.5 | 65 | 35 |
| 12 | 0.5 | 2.5 | 0.04 | 6 | 0.4 | 3.2 | 6.4 | 93.6 |
| 17 | 0.05 | 0.25 | 0.02 | 30 | 2 | 16 | 32 | 68 |

EXAMPLE 20

Synergistic Composition No. VIII $n=2$ the ratio of the components: $C_1:B_1=50:50$ The results relating to the antimicrobial activity of the composition are summarized in Table VIII. (The abbreviations are the same as in Example 13 except that component $C_1$ is used instead of component $A_1$.)

TABLE VIII

| The strains examined | I | II | III | IV | V | VI | VII | VIII |
|---|---|---|---|---|---|---|---|---|
| 1 | 0.075 | 0.5 | 0.08 | 53.3 | 8 | 30.6 | 61.3 | 38.7 |
| 2 | 0.05 | 0.1 | 0.03 | 30 | 15 | 22.5 | 45 | 55 |
| 3 | 0.05 | 0.1 | 0.03 | 30 | 15 | 22.5 | 45 | 55 |
| 4 | 0.05 | 0.25 | 0.03 | 30 | 6 | 18 | 36 | 64 |
| 5 | 0.05 | 0.1 | 0.03 | 30 | 15 | 22.5 | 45 | 55 |
| 6 | 0.025 | 0.1 | 0.02 | 40 | 10 | 25 | 50 | 50 |
| 7 | 0.025 | 0.25 | 0.02 | 40 | 4 | 22 | 44 | 66 |
| 8 | 0.05 | 0.5 | 0.03 | 30 | 3 | 16.5 | 33 | 67 |
| 9 | 0.75 | 2.5 | 0.8 | 53.3 | 16 | 34.6 | 69.3 | 30.7 |
| 10 | 0.075 | 0.5 | 0.1 | 66.6 | 10 | 38.3 | 76.6 | 23.4 |
| 11 | 0.25 | 1 | 0.06 | 12 | 3 | 7.5 | 15 | 85 |
| 12 | 0.5 | 2.5 | 0.03 | 3 | 0.6 | 1.8 | 3.6 | 96.4 |
| 13 | 0.025 | 0.1 | 0.02 | 40 | 10 | 25 | 50 | 50 |
| 15 | 0.025 | 0.25 | 0.02 | 40 | 4 | 22 | 44 | 66 |
| 16 | 0.025 | 0.25 | 0.02 | 40 | 4 | 22 | 44 | 66 |
| 17 | 0.05 | 0.25 | 0.02 | 20 | 4 | 12 | 24 | 76 |
| 18 | 0.075 | 0.25 | 0.08 | 53.3 | 10 | 34.6 | 69.3 | 30.7 |

EXAMPLE 21

Synergistic Composition No. IX $n=2$ the ratio of the components: $C_1:B_1=25:75$ The results relating to the antimicrobial activity of the composition are summarized in Table IX. (The abbreviations are the same as in Example 13 except that component $C_1$ is used instead of component $A_1$.)

TABLE IX

| The strains examined | I | II | III | IV | V | VI | VII | VIII |
|---|---|---|---|---|---|---|---|---|
| 1 | 0.075 | 0.5 | 0.1 | 33.3 | 15 | 24.1 | 48.3 | 51.7 |
| 2 | 0.05 | 0.5 | 0.04 | 20 | 6 | 13 | 26 | 74 |
| 3 | 0.05 | 0.1 | 0.04 | 20 | 30 | 25 | 50 | 50 |
| 4 | 0.05 | 0.25 | 0.08 | 40 | 8 | 24 | 48 | 52 |
| 6 | 0.025 | 0.1 | 0.02 | 20 | 15 | 17.5 | 35 | 65 |
| 7 | 0.025 | 0.25 | 0.03 | 30 | 9 | 19.5 | 39 | 61 |
| 8 | 0.05 | 0.5 | 0.06 | 30 | 9 | 19.5 | 39 | 61 |
| 11 | 0.25 | 1 | 0.4 | 40 | 30 | 35 | 70 | 30 |
| 12 | 0.5 | 2.5 | 0.1 | 5 | 3 | 4 | 8 | 92 |
| 13 | 0.025 | 0.1 | 0.02 | 20 | 15 | 17.5 | 35 | 65 |
| 14 | 0.025 | 0.25 | 0.03 | 30 | ·9 | 19.5 | 39 | 61 |
| 15 | 0.025 | 0.25 | 0.03 | 30 | 9 | 19.5 | 39 | 61 |
| 16 | 0.025 | 0.25 | 0.03 | 30 | 9 | 19.5 | 39 | 61 |
| 17 | 0.05 | 0.25 | 0.03 | 15 | 9 | 12 | 24 | 76 |
| 18 | 0.075 | 0.25 | 0.1 | 33.3 | 30 | 31.6 | 63.3 | 36.7 |
| 19 | 0.01 | 0.05 | 0.02 | 50 | 30 | 40 | 80 | 20 |
| 20 | 0.01 | 0.075 | 0.02 | 50 | 20 | 35 | 70 | 30 |

EXAMPLE 22

Synergistic Composition No. X $n=3$ the ratio of the components: $A_1:C_1:B_1=40:30:30$ The results relating to the antimicrobial acitivity of the composition are summarized in Table X. The abbreviations of Table X are as follows: Coloumn I: MIC value of component $A_1$ ($\lambda$g/ml)

Column II: MIC value of component $C_1$ ($\mu$g/ml)

Column III: MIC value of component $B_1$ ($\mu$g/ml)

Column IV: MIC value of the composition comprising components $A_1+B_1+C_1$

Column V: the amount of $A_1$ being in the composition related to the MIC value of component $A_1$ (%)

Column VI: the amount of $C_1$ being in the composition related to the MIC value of component $C_1$ (%)

Column VII: the amount of component $B_1$ being in the composition related to the MIC value of component $B_1$ (%)

Column VIII: $(V+VI+VII)/n$

Column IX: the additive portion of the antimicrobial activity $(V+VI+VII)$

Column X: the synergistic portion of the antimicrobial activity $(100\%-IX)$

TABLE X

| The strains examined | I | II | III | IV | V | VI | VII | VIII | IX | X |
|---|---|---|---|---|---|---|---|---|---|---|
| 1 | 0.25 | 0.075 | 0.5 | 0.1 | 16 | 40 | 6 | 20.6 | 62 | 38 |
| 2 | 0.05 | 0.05 | 0.1 | 0.05 | 40 | 30 | 15 | 28.3 | 85 | 15 |
| 5 | 0.25 | 0.05 | 0.1 | 0.05 | 8 | 30 | 15 | 17.6 | 53 | 47 |
| 6 | 0.25 | 0.025 | 0.1 | 0.03 | 4.8 | 36 | 9 | 16.6 | 49.8 | 50 |
| 7 | 0.75 | 0.025 | 0.25 | 0.05 | 2.6 | 60 | 6 | 22.8 | 68.6 | 31.4 |
| 8 | 0.25 | 0.05 | 0.5 | 0.08 | 12.8 | 48 | 4.8 | 21.8 | 65.6 | 34.4 |
| 10 | 0.75 | 0.075 | 0.5 | 0.08 | 4.2 | 32 | 4.8 | 13.6 | 41 | 59 |
| 11 | 1 | 0.25 | 1 | 0.08 | 3.2 | 9.6 | 2.4 | 5.1 | 15.2 | 84.8 |
| 12 | 2.5 | 0.5 | 1 | 0.6 | 9.6 | 36 | 7.2 | 17.6 | 52.8 | 47.2. |
| 13 | 0.25 | 0.025 | 2.5 | 0.3 | 4.8 | 36 | 9 | 16.6 | 49.8 | 50.2 |
| 14 | 0.25 | 0.025 | 0.1 | 0.03 | 4.8 | 36 | 3.6 | 14.8 | 44.4 | 55.6 |

TABLE X-continued

| The strains examined | I | II | III | IV | V | VI | VII | VIII | IX | X |
|---|---|---|---|---|---|---|---|---|---|---|
| 15 | 0.25 | 0.025 | 0.25 | 0.03 | 4.8 | 36 | 3.6 | 14.8 | 44.4 | 55.6 |
| 16 | 0.25 | 0.025 | 0.25 | 0.05 | 8 | 60 | 6 | 24.6 | 74 | 26 |
| 17 | 0.25 | 0.05 | 0.25 | 0.02 | 3.2 | 12 | 2.4 | 5.8 | 17.6 | 82.4 |
| 20 | 0.05 | 0.01 | 0.075 | 0.01 | 8 | 30 | 4 | 14 | 42 | 58 |

EXAMPLE 23

Synergistic Composition No. XI $n = 3$ the ratio of the components: A:C:B = 50:25:25

The results relating to the antimicrobial activity of the composition are summarized in Table XI. (The abbreviations of the table are the same as in Example 22.)

TABLE XI

| The strains examined | I | II | III | IV | V | VI | VII | VIII | IX | X |
|---|---|---|---|---|---|---|---|---|---|---|
| 1 | 0.25 | 0.075 | 0.5 | 0.1 | 20 | 33.3 | 5 | 19.4 | 58.3 | 41.7 |
| 3 | 0.25 | 0.05 | 0.1 | 0.08 | 16 | 40 | 20 | 25.3 | 76 | 24 |
| 4 | 0.25 | 0.05 | 0.25 | 0.1 | 20 | 50 | 10 | 26.6 | 80 | 20 |
| 5 | 0.25 | 0.05 | 0.1 | 0.04 | 8 | 20 | 10 | 12.6 | 38 | 62 |
| 6 | 0.25 | 0.025 | 0.1 | 0.04 | 8 | 40 | 10 | 19.3 | 58 | 42 |
| 7 | 0.75 | 0.025 | 0.25 | 0.05 | 3.3 | 50 | 5 | 19.4 | 58.3 | 41.7 |
| 8 | 0.25 | 0.05 | 0.5 | 0.05 | 10 | 25 | 2.5 | 12.5 | 37.5 | 62.5 |
| 9 | 2.5 | 0.75 | 2.5 | 1 | 20 | 33.3 | 10 | 21.1 | 63.3 | 36.7 |
| 10 | 0.75 | 0.075 | 0.5 | 0.1 | 6.6 | 33.3 | 5 | 14.9 | 44.9 | 55.1 |
| 11 | 1 | 0.2 | 1 | 0.4 | 20 | 40 | 10 | 23.3 | 70 | 30 |
| 12 | 2.5 | 0.5 | 2.5 | 0.4 | 8 | 20 | 4 | 10.6 | 32 | 68 |
| 13 | 0.25 | 0.025 | 0.1 | 0.04 | 8 | 40 | 10 | 19.3 | 58 | 42 |
| 14 | 0.25 | 0.025 | 0.25 | 0.06 | 12 | 60 | 6 | 26 | 78 | 22 |
| 15 | 0.25 | 0.025 | 0.25 | 0.03 | 6 | 30 | 3 | 13 | 39 | 61 |
| 16 | 0.25 | 0.025 | 0.25 | 0.05 | 10 | 50 | 5 | 21.6 | 65 | 35 |
| 17 | 0.25 | 0.05 | 0.25 | 0.05 | 10 | 25 | 5 | 13.3 | 40 | 60 |
| 18 | 0.5 | 0.075 | 0.25 | 0.08 | 8 | 26.6 | 8 | 14.2 | 42.6 | 57.3 |
| 19 | 0.075 | 0.01 | 0.05 | 0.02 | 13.3 | 50 | 10 | 24.4 | 73.3 | 26.7 |
| 20 | 0.05 | 0.01 | 0.075 | 0.02 | 20 | 50 | 6.6 | 25.5 | 76.6 | 23.4 |

EXAMPLE 24

Synergistic Composition No. XII $n = 3$ the ratio of the components: A:C:B = 60:20:20

The results relating to the antimicrobial activity of the composition are summarized in Table XII. The abbreviations of the table are the same as in Example 22.)

TABLE XII

| The strains examined | I | II | III | IV | V | VI | VII | VIII | IX | X |
|---|---|---|---|---|---|---|---|---|---|---|
| 1 | 0.25 | 0.075 | 0.5 | 0.08 | 19.2 | 21.3 | 3.2 | 14.6 | 43.7 | 56.3 |
| 4 | 0.25 | 0.05 | 0.25 | 0.1 | 24 | 40 | 8 | 24 | 72 | 28 |
| 5 | 0.25 | 0.05 | 0.1 | 0.04 | 9.6 | 16 | 7.3 | 11 | 32.9 | 67.1 |
| 6 | 0.25 | 0.025 | 0.1 | 0.03 | 7.2 | 24 | 6 | 12.4 | 37.2 | 62.8 |
| 7 | 0.75 | 0.025 | 0.25 | 0.05 | 4 | 40 | 4 | 24 | 48 | 52 |
| 8 | 0.25 | 0.05 | 0.5 | 0.04 | 9.6 | 16 | 1.6 | 9.1 | 27.2 | 72.8 |
| 9 | 2.5 | 0.75 | 2.5 | 1 | 24 | 26.7 | 8 | 19.6 | 58.7 | 41.3 |
| 10 | 0.75 | 0.075 | 0.5 | 0.03 | 2.4 | 8 | 1.2 | 3.9 | 11.6 | 88.4 |
| 11 | 1 | 0.25 | 1 | 0.4 | 24 | 32 | 8 | 21.3 | 64 | 36 |
| 12 | 2.5 | 0.5 | 2.5 | 0.4 | 9.6 | 16 | 3.2 | 9.6 | 28.8 | 71.2 |
| 13 | 0.25 | 0.025 | 0.1 | 0.04 | 9.6 | 32 | 8 | 16.5 | 49.6 | 50.4 |
| 14 | 0.25 | 0.025 | 0.25 | 0.04 | 9.6 | 32 | 3.2 | 14.9 | 44.8 | 55.2 |
| 15 | 0.25 | 0.025 | 0.25 | 0.05 | 12 | 40 | 4 | 18.6 | 56 | 44 |
| 16 | 0.25 | 0.025 | 0.25 | 0.04 | 9.6 | 32 | 3.2 | 14.9 | 44.8 | 55.2 |
| 17 | 0.25 | 0.05 | 0.25 | 0.04 | 9.6 | 16 | 3.2 | 9.6 | 28.8 | 71.2 |
| 19 | 0.075 | 0.01 | 0.05 | 0.02 | 16 | 40 | 8 | 21.3 | 64 | 36 |
| 20 | 0.05 | 0.01 | 0.075 | 0.02 | 24 | 40 | 5.3 | 23.1 | 69.3 | 30.7 |

EXAMPLE 25

Synergistic Composition No. XIII $n = 3$ the ratio of the components: $A_1:C_1:B_1 = 70:10:20$ The results relating to the antimicrobial activity of the composition are summarized in Table XIII. (The abbreviations of the table are the same as in Example 22.)

TABLE XIII

| The strains examined | I | II | III | IV | V | VI | VII | VIII | IX | X |
|---|---|---|---|---|---|---|---|---|---|---|
| 2 | 0.05 | 0.05 | 0.1 | 0.04 | 56 | 8 | 8 | 24 | 72 | 28 |
| 3 | 0.25 | 0.05 | 0.1 | 0.1 | 28 | 20 | 20 | 22.6 | 68 | 32 |
| 4 | 0.25 | 0.05 | 0.25 | 0.1 | 28 | 20 | 8 | 18.6 | 56 | 44 |
| 5 | 0.25 | 0.05 | 0.1 | 0.05 | 14 | 10 | 10 | 11.3 | 34 | 66 |
| 6 | 0.25 | 0.025 | 0.1 | 0.03 | 8.4 | 12 | 6 | 8.8 | 26.4 | 73.6 |
| 7 | 0.75 | 0.025 | 0.25 | 0.04 | 3.7 | 16 | 3.2 | 7.6 | 22.9 | 77.1 |
| 8 | 0.25 | 0.05 | 0.5 | 0.08 | 22.4 | 16 | 3.2 | 13.8 | 41.6 | 58.4 |
| 10 | 0.75 | 0.075 | 0.5 | 0.2 | 18.6 | 26.6 | 8 | 17.7 | 53.2 | 46.8 |
| 11 | 1 | 0.25 | 1 | 0.4 | 28 | 16 | 8 | 17.3 | 52 | 48 |
| 12 | 2.5 | 0.5 | 2.5 | 0.6 | 16.8 | 12 | 4.8 | 11.2 | 33.6 | 66.4 |
| 13 | 0.25 | 0.025 | 0.1 | 0.03 | 8.4 | 12 | 6 | 8.8 | 26.4 | 73.6 |
| 14 | 0.25 | 0.025 | 0.25 | 0.04 | 11.2 | 16 | 3.2 | 10.1 | 30.4 | 69.6 |
| 15 | 0.25 | 0.025 | 0.25 | 0.06 | 16.8 | 24 | 4.8 | 15.2 | 45.6 | 54.4 |
| 16 | 0.25 | 0.025 | 0.25 | 0.03 | 8.4 | 12 | 2.4 | 7.6 | 22.8 | 77.2 |
| 17 | 0.25 | 0.5 | 0.25 | 0.04 | 11.2 | 8 | 3.2 | 7.4 | 22.4 | 77.6 |
| 18 | 0.5 | 0.075 | 0.25 | 0.2 | 28 | 26.6 | 16 | 23.5 | 70.6 | 29.4 |
| 19 | 0.075 | 0.01 | 0.05 | 0.02 | 18.6 | 20 | 8 | 15.3 | 46.6 | 53.4 |
| 20 | 0.05 | 0.01 | 0.075 | 0.01 | 14 | 10 | 2.6 | 8.8 | 26.6 | 73.4 |

The following examples relate to pharmaceutical compositions comprising the individual components of primycin or the synergistic mixture thereof as active ingredient. The pharmaceutical compositions are prepared in a manner known per se.

Under the term "active ingredient" the isolated components of primycin or a mixture thereof is understood.

EXAMPLE 26

| Dusting powder No. I | |
|---|---|
| Active ingredient | 1.0 g |
| Cyclodextrine | 9.0 g |
| | 10.0 g |

EXAMPLE 27

| Dusting powder No. II | |
|---|---|
| Active ingredient | 1.0 g |
| Amylum non mucilaginosum | 9.0 g |
| | 10.0 g |

EXAMPLE 28

| Dusting powder No. III | |
|---|---|
| Active ingredient | 1.0 g |
| Aetheroleum lavandulae | 0.02 g |
| Acid silicicum colloidale | 0.10 g |
| Magnesium stearinicum | 0.10 g |
| Zincum oxidatum | 0.20 g |
| Bolus alba | 0.50 g |
| Magnesium carbonicum hydroxidatum | 1.00 g |
| Cyclodextrine | 7.08 g |
| | 10.0 g |

EXAMPLE 29

| Sprayable dusting powder | |
|---|---|
| Active ingredient | 0.20 g |
| Isopropylmyristate | 1.00 g |
| Freon 11/12 5050 (carrier gas) | 98.80 g |
| | 100.00 g |

EXAMPLE 30

| Aqueous aerosol | |
|---|---|
| Active ingredient | 0.5 g |
| Ethanol (62.5% by volume) | 10.0 g |
| water | 39.5 g |
| carrier gas | 50.0 g |
| | 100.0 g |

EXAMPLE 31

| Sprayable Surgical plaster | |
|---|---|
| Active ingredient | 0.1 g |
| polyvinyl-pyrrolidone | 1.50 g |
| ethanol (62.5% by volume) | 48.40 g |
| propellant gas | 50.00 g |

EXAMPLE 32

| Gel | |
|---|---|
| Active ingredient | 0.20 g |
| Lidocain | 2.00 g |
| Chlorophyl | 0.005 g |
| Menthol | 0.20 g |
| Carbopol 940 | 1.20 g |
| Triethanolamine | 1.50 g |
| Tween 20 | 1.50 g |
| Isoadipat | 5.00 g |
| Ethanol 96% | 50.00 g |
| Aqua dest. ad | 100.00 g |

The ingredients are mixed and filled into a flask.

EXAMPLE 33

| Ointment | |
|---|---|
| Active ingredient | 2.00 g |
| Oleum paraffini | 33.0 g |
| Vaselinum album | 31.0 g |

-continued

| Ointment | |
|---|---|
| Ethanol 96% | 20.0 g |
| Tween 60 | 9.0 g |
| Wool fat | 5.0 g |
| | 100.0 g |

The ingredients are mixed and filled into a bottle or jar.

EXAMPLE 34

| Eye-salve | |
|---|---|
| Active ingredient | 0.04 g |
| Ethanol 62.5 by volume | 0.08 g |
| Distilled water | 3.16 g |
| Beeswax | 300.00 g |
| Cholesterol | 25.00 g |
| Sterile castor oil to | 1000.0 g |

EXAMPLE 35

| Ointment washable by water No. 1 | |
|---|---|
| Active ingredient | 2.0 g |
| Tween 60 | 5.0 g |
| Liquid paraffin | 5.0 g |
| Cetylstearylalcohol | 15.0 g |
| White vaseline | 25.0 g |
| Distilled water to | 100.0 g |

EXAMPLE 36

| Ointment washable by water No. II | |
|---|---|
| Active ingredient | 0.100 g |
| Ethanol 62.5% by volume | 2.000 g |
| Water | 7.900 g |
| Sorboxaethene stearate | 3.600 g |
| Liquid paraffin | 3.600 g |
| Cetylstearylalcohol | 10.800 g |
| White vaseline | 18.000 g |
| Propyl-paraoxybenzoate | 0.054 g |
| Methylparaoxybenzoate | 0.126 g |
| Ethanol, 96% by volume | 2.930 g |
| Lidocainum chloride | 1.000 g |
| Distilled water to | 100.000 g |

EXAMPLE 37

| Eye-salve | |
|---|---|
| Active ingredient | 0.02 g |
| Sodium hydrogencarbonate | 18.00 g |
| Viscous solvent (4 g of methylcellulose +3.5 g of NaCl +distilled water ad 510 g) | 510.00 g |
| Phenyl-mercury-borate, (0.1%) | 15.1 g |
| distilled water to | 1000.0 g |

EXAMPLE 38

| Oily eye-salve | |
|---|---|
| Active ingredient | 0.02 g |
| Ethanol, 62.5% by volume | 0.40 g |
| Distilled water | 1.58 g |
| Cholesterol | 25.00 g |
| Sterile castor oil to | 100.00 g |

EXAMPLE 39

| Vaginal suppository | |
|---|---|
| Active ingredient | 0.02 g |
| Ethanol, 62.5% by volume | 0.262 g |
| Gelatine | 1.40 g |
| Sodium-acetate | 0.26 g |
| Glycerine | 4.50 g |
| Distilled water to | 9.50 g |

EXAMPLE 40

Antimicrobial Bandage

A solution of the isolated components of primycin or a mixture thereof is made preferably with ethanol and bandages, e.g. mull-sheet is saturated with it, thereafter the bandage is packed and sterilized in a usual way.

The sterile, antimicrobial bandage thus prepared can be used up at any time.

We claim:

1. Oxypricin of the formula II

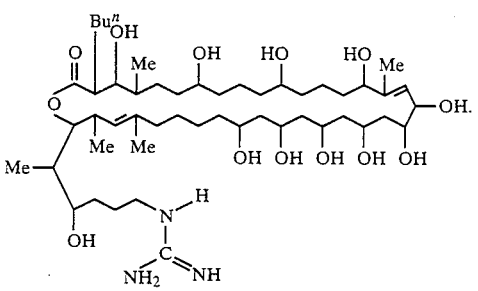

having an $R_f$ value of 0.35 developed on thin-layer chromatoplate with a combined solvent system and having a molar weight of 946 determined by FAB-MS method or a pharmaceutically acceptable salt thereof.

2. A pharmaceutically acceptable salt of Oxypricin as defined in claim 1 formed with an organic acid or an inorganic acid.

3. A pharmaceutically acceptable salt of Oxypricin as defined in claim 2 formed with an organic acid selected from the group consisting of a $C_1$ to $C_{16}$ aliphatic organic acid unsubstituted or halo-substituted, an aromatic carboxylic acid, and an organic sulfonic acid.

4. A pharmaceutically acceptable salt of Oxypricin as defined in claim 2 formed with an inorganic acid selected from the group consisting of sulfuric acid and a hydrohalogenic acid.

5. A pharmaceutically acceptable salt of Oxypricin as defined in claim 1 which is the acetate, monochloroacetate, sulfate or formate salt of Oxypricin.

* * * * *